United States Patent
Chen

(10) Patent No.: US 9,880,104 B2
(45) Date of Patent: Jan. 30, 2018

(54) PARTICULATE MATTER DETECTION APPARATUS

(71) Applicant: SHENZHEN CHINA STAR OPTOELECTRONICS TECHNOLOGY CO., LTD., Shenzhen, Guangdong (CN)

(72) Inventor: Hui Chen, Guangdong (CN)

(73) Assignee: SHENZHEN CHINA STAR OPTOELECTRONICS TECHNOLOGY CO., LTD, Shenzhen (CN)

( * ) Notice: Subject to any disclaimer, the term of this patent is extended or adjusted under 35 U.S.C. 154(b) by 186 days.

(21) Appl. No.: 13/983,602

(22) PCT Filed: Jun. 29, 2013

(86) PCT No.: PCT/CN2013/078487
§ 371 (c)(1),
(2) Date: Aug. 5, 2013

(87) PCT Pub. No.: WO2014/173010
PCT Pub. Date: Oct. 30, 2014

(65) Prior Publication Data
US 2017/0184510 A1    Jun. 29, 2017

(30) Foreign Application Priority Data
Apr. 26, 2013    (CN) .......................... 2013 1 0150683

(51) Int. Cl.
*G01B 11/14* (2006.01)
*G01N 21/88* (2006.01)
(Continued)

(52) U.S. Cl.
CPC ......... *G01N 21/8806* (2013.01); *G01N 21/47* (2013.01); *G01N 21/95* (2013.01);
(Continued)

(58) Field of Classification Search
CPC .. G01N 21/94; G01N 21/8806; G06T 7/0004; H04N 5/372; G06F 3/14; G08B 21/18
(Continued)

(56) References Cited

U.S. PATENT DOCUMENTS

| 3,809,907 | A | * | 5/1974 | Schuller | ................ | B29C 43/245 |
| | | | | | | 250/548 |
| 5,206,703 | A | * | 4/1993 | Holmes | .................. | G01B 11/14 |
| | | | | | | 356/625 |
| 2008/0110205 | A1 | * | 5/2008 | Adriaansen | .......... | B65G 49/065 |
| | | | | | | 65/29.12 |
| 2009/0168056 | A1 | * | 7/2009 | Nakamura | ......... | G01N 21/8901 |
| | | | | | | 356/237.4 |
| 2009/0274828 | A1 | * | 11/2009 | Park | .......................... | G03F 7/16 |
| | | | | | | 427/8 |
| 2013/0291593 | A1 | * | 11/2013 | Roh | ..................... | G01N 21/958 |
| | | | | | | 65/29.12 |

(Continued)

FOREIGN PATENT DOCUMENTS

| CN | 1757440 A | 4/2006 |
| CN | 1916610 A | 2/2007 |

(Continued)

OTHER PUBLICATIONS

Chenguang Tang, the International Searching Authority written comments, Jan. 2014, CN.

*Primary Examiner* — Hoa Pham

(57) ABSTRACT

The present invention discloses a particulate matter detection apparatus, which comprises a gantry, a protect bar, a light emitter and a light receiver, there is a gap between the protect bar and the glass substrate to be detected, the gap has a predetermined height, the light emitter and the light receiver are located at the opposite sides of the glass substrate respectively. The particulate matter detection apparatus can detect particulate matter on the surface of glass substrates, such that the mask will not scraped and thus damaged by particulate matter.

10 Claims, 2 Drawing Sheets

(51) Int. Cl.
   *G01N 21/95* (2006.01)
   *G01N 21/47* (2006.01)
   G01N 21/01 (2006.01)
   G01N 21/17 (2006.01)

(52) U.S. Cl.
   CPC ............... *G01N 2021/0106* (2013.01); *G01N 2021/1765* (2013.01); *G01N 2021/4735* (2013.01); *G01N 2021/8841* (2013.01); *G01N 2021/9513* (2013.01)

(58) Field of Classification Search
   USPC ......... 356/237.1–237.5, 239.1, 239.2, 239.3, 356/625–632
   See application file for complete search history.

(56) References Cited

U.S. PATENT DOCUMENTS

2015/0219450 A1* 8/2015 Hohshi ................. G01B 15/02
                                                  378/50
2017/0108447 A1* 4/2017 Lin ....................... G01N 21/94

FOREIGN PATENT DOCUMENTS

| CN | 1940537 A | 4/2007 |
| CN | 101848884 A | 9/2010 |
| CN | ON102636498 A | 8/2012 |
| JP | 2000-24571 A | 1/2000 |
| JP | 2000-230910 A | 8/2000 |
| JP | 2002-1195 A | 1/2002 |
| JP | 2007-85960 A | 4/2007 |
| JP | 2009-174957 A | 8/2009 |

\* cited by examiner

PARTICULATE MATTER DETECTION APPARATUS

FIELD OF THE INVENTION

The present invention relates to the manufacturing technology of liquid crystal displays, and more particularly to a particulate matter detection apparatus.

BACKGROUND OF THE INVENTION

Nowadays, LCD (liquid crystal display) TV, PC, Monitors, display devices are widely used. In the manufacturing of LCD modules, particulate matter (PM) has great adverse effect on the quality of LCD modules. For example, in the manufacturing process of thin film transistor (TFT), the exposure machine may be near to the surface of the glass substrate (the distance there-between is about 200 micron), especially when the area of the mask is large. In such situation, if the particulate matter on the surface of the glass substrate adheres to the mask, the mask may be damaged.

SUMMARY OF THE INVENTION

The present invention provides a particulate matter detection apparatus to solve the mentioned problem above.

The present invention is realized in such a way that: a particulate matter detection apparatus, comprising a gantry, a protect bar, a light emitter and a light receiver, wherein the protect bar is coupled to the gantry, there is a gap between the protect bar and the glass substrate to be detected, the gap has a predetermined height, the light emitter and the light receiver are located at the opposite sides of the glass substrate respectively, the light emitter is configured to emit light towards the gap, the light receiver is configured to receive the light passing through the gap.

According to an embodiment disclosed herein, the predetermined height is 100 micron to 800 micron.

According to another embodiment disclosed herein, the predetermined height is 200 micron.

According to another embodiment disclosed herein, the light emitter is laser transmitter.

According to another embodiment disclosed herein, the light receiver is CCD image sensor.

According to another embodiment disclosed herein, the particulate matter detection apparatus further comprises an actuator and a controller, the actuator serves to actuate the protect bar, the light emitter and the light receiver such that the protect bar, the light emitter and the light receiver move synchronously, the controller serves to control the protect bar, the light emitter and the light receiver.

According to another embodiment disclosed herein, the particulate matter detection apparatus further comprises an actuator and a controller, the actuator serves to actuate the protect bar, the light emitter and the light receiver such that the protect bar, the light emitter and the light receiver move synchronously, the controller serves to control the protect bar, the light emitter and the light receiver.

According to another embodiment disclosed herein, the particulate matter detection apparatus further comprises an actuator and a controller, the actuator serves to actuate the protect bar, the light emitter and the light receiver such that the protect bar, the light emitter and the light receiver move synchronously, the controller serves to control the protect bar, the light emitter and the light receiver.

According to another embodiment disclosed herein, the particulate matter detection apparatus further comprises an actuator and a controller, the actuator serves to actuate the protect bar, the light emitter and the light receiver such that the protect bar, the light emitter and the light receiver move synchronously, the controller serves to control the protect bar, the light emitter and the light receiver.

According to another embodiment disclosed herein, the particulate matter detection apparatus further comprises an alarm; the alarm is electrically connected to the controller, such that when the light receiver detects particulate matter, the alarm is enabled.

According to another embodiment disclosed herein, the protect bar is coupled to the gantry by multiple bolts, the protect bar is provided with multiple counterbored through holes, the head portions of the multiple bolts are hooked in the multiple counterbored through holes, the threaded portions of the multiple bolts are engaged with the gantry.

According to another embodiment disclosed herein, the particulate matter detection apparatus further comprises multiple compression springs which surround the multiple bolts, the compression springs abut against the bottom surface of the gantry and the top surface of the protect bar.

According to another embodiment disclosed herein, the particulate matter detection apparatus further comprises multiple vibration detection elements, the multiple vibration detection elements serve to detect the vibration of the protect bar.

According to yet another embodiment disclosed herein, the multiple vibration detection elements are electronic digital display height gauges, the multiple vibration detection elements serve to measure the height of the top surface of the protect bar.

According to the present invention, a particulate matter detection apparatus comprises a gantry, a protect bar, a light emitter and a light receiver, there is a gap between the protect bar and the glass substrate to be detected, the light emitter and the light receiver are located at the opposite sides of the glass substrate respectively, the light emitter is configured to emit light towards the gap, the particulate matter detection apparatus can detect particulate matter on the surface of glass substrates, such that the mask will not scraped and thus damaged by particulate matter.

For more clearly and easily understanding above content of the present invention, the following text will take a preferred embodiment of the present invention with reference to the accompanying drawings for detail description as follows.

BRIEF DESCRIPTION OF THE DRAWINGS

The drawings described herein are for illustration purposes only and are not intended to limit the scope of the present disclosure in any way.

DETAILED DESCRIPTION OF PREFERRED EMBODIMENTS

The following detailed description of every embodiment with reference to the accompanying drawings is used to exemplify a specific embodiment, which may be carried out in the present invention. Directional terms mentioned in the present invention, such as "top", "bottom", "front", "rear", "left", "right", "up", "down", "inside", "outside", "side" etc., are only used with reference to the orientation of the accompanying drawings. Therefore, the used directional terms are intended to illustrate, but not to limit, the present invention. Also the following description is merely exemplary in nature and is not intended to limit the present disclosure, application, or uses. Besides, the term "particulate matter" used herein included foreign matters not belonging naturally in the place where found.

The particulate matter detection apparatus according to the present invention may be used to detect particulate matter on the surface of glass substrates 100 in the manufacturing process of thin film transistor (TFT), such that the mask will not scraped and thus damaged by particulate matter. The particulate matter may be all kinds of solid particles such as dust.

Figure 1:
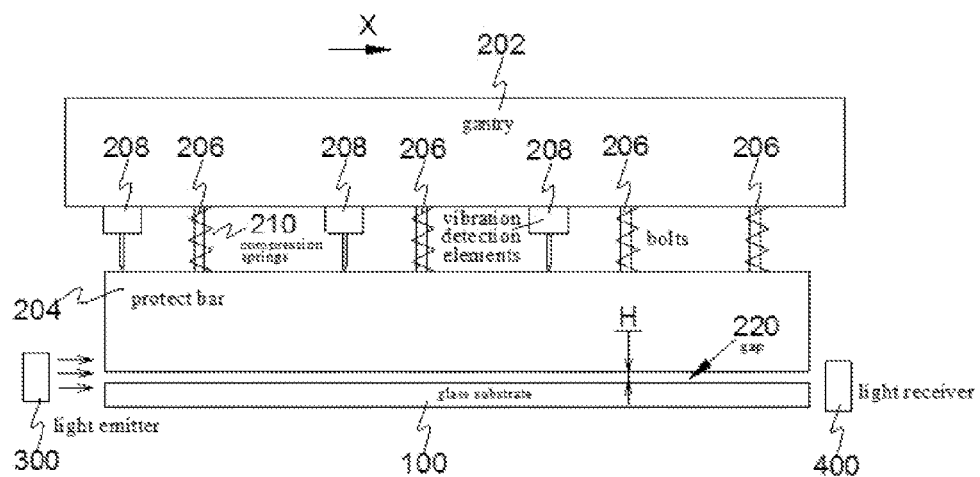
FIG. 1 is a schematic front view of the particulate matter detection apparatus according to an embodiment of the present invention.
Figure 2:
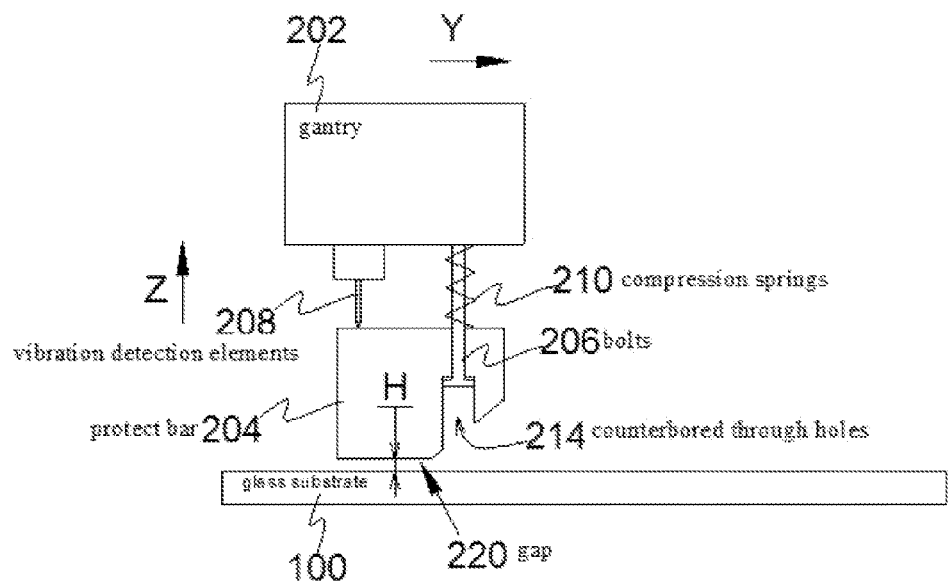
FIG. 2 is a schematic side view of the particulate matter detection apparatus in FIG. 1.
Figure 3:
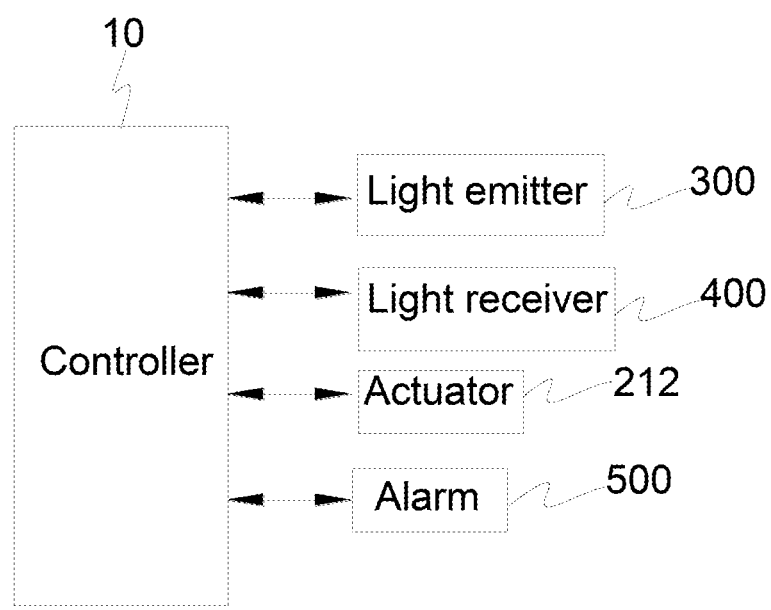
FIG. 3 is the schematic electrical control diagram of the particulate matter detection apparatus in FIG. 1.

As shown in FIG. 1 and FIG. 2, the particulate matter detection apparatus comprises a gantry 202, a protect bar 204, a light emitter 300 and a light receiver 400. The protect bar 204 is coupled (movably connected) to the gantry 202. There is a gap 220 between the protect bar 204 and the glass substrate 100 to be detected. The gap 220 has a predetermined height H.

The predetermined height H is 100 micron to 800 micron. Preferably, the predetermined height H is 200 micron. The predetermined height H of the gap 220 may correspond with the mean value of the height of typical particulate matter found in the manufacturing process of thin film transistor (TFT).

As shown in FIG. 1, the light emitter 300 and the light receiver 400 are located at the opposite sides of the glass substrate 100 respectively. The light emitter 300 is at the left side of the glass substrate 100 while the light receiver 400 is at the right side of the glass substrate 100. The light emitter 300 is configured to emit light towards and into the gap 220. The light receiver 400 is configured to receive the light passing through the gap 220. When the light receiver 400 is shaded from the light by particulate matter completely or partly, it is considered that there is particulate matter. When the light receiver 400 is not shaded from the light by particulate matter, it is considered that there is no particulate matter. In this way, on the basis of shading degree, the existence and the size (including height and width) of particulate matter can be deduced. The light emitter 300 may be laser transmitter; while the light receiver 400 may be CCD (charge-coupled device) image sensor.

In some embodiments of the present invention, the particulate matter detection apparatus further comprises an actuator 212 and a controller 10. The actuator 212 serves to actuate the protect bar 204, the light emitter 300 and the light receiver 400 such that the protect bar 204, the light emitter 300 and the light receiver 400 move synchronously. The actuator 212 may comprise motors. The controller 10 serves to control the protect bar 204, the light emitter 300 and the light receiver 400. In detection, the protect bar 204, the light emitter 300 and the light receiver 400 move synchronously above the glass substrate 100. The glass substrate 100 may be stationary, while the light emitter 300 may scan on the glass substrate 100 quickly along the longitudinal direction Y or lateral direction X.

Moreover, the particulate matter detection apparatus may further comprise an alarm 500. The alarm 500 is electrically connected to the controller 10, such that when the light receiver 400 detects particulate matter, the alarm 500 is enabled. The alarm 500 serves to warn of danger by means of a sound or signal.

When the scanning light is emitted, the light receiver 400 will only receive a part of light if there is the particular matter in the gap 220. The digital signal (for example in the form of voltage) of the light intensity can be analyzed by the light receiver 400 and the size of the particular matter can be calculated. Furthermore, the effective width of detection of the light receiver 400 may be set and changed as needed, so as to detect different kinds of particular matter.

The light receiver 400 (CCD image sensor) can convert the light emitted by the light emitter 300 into digital value. And the light receiver 400 (CCD image sensor) may divide the light emitted by the light emitter 300 into several square-shaped areas along the vertical direction Z and the longitudinal direction Y. When there is no particular matter, the light receiver 400 will receive the light from the light emitter 300 substantially completely, and the digital value of the light receiver 400 is full and stable. When there is particular matter, the light receiver 400 will receive a part of the light from the light emitter 300, and the digital value of the light receiver 400 will drop. When the digital value of the light receiver 400 drops dramatically, the alarm 500 is enabled by the controller 10, such that the operator will handle accordingly to remove the particular matter.

As shown in FIG. 1 and FIG. 2, the protect bar 204 is coupled to the gantry 202 by multiple bolts 206. The protect bar 204 is provided with multiple counterbored through holes 214. The head portions of the multiple bolts 206 are hooked in the multiple counterbored through holes 214. The threaded portions of the multiple bolts 206 are screwed with the gantry 202. The number of the bolts 206 and the through holes 214 are four. Furthermore, the particulate matter detection apparatus further comprises multiple compression springs 210. The compression springs 210 surround the multiple bolts 206. The compression springs 210 abut against the bottom surface of the gantry 202 and the top surface of the protect bar 204, as shown in FIG. 2. By means of compression springs 210, the protect bar 204 has the DOF (Degree of Freedom) of motion along the vertical direction Z. In other words, the protect bar 204 is allowed to move slightly along the vertical direction Z.

In this embodiment, the particulate matter detection apparatus further comprises multiple vibration detection elements 208. The multiple vibration detection elements 208 serve to detect the vibration of the protect bar 204. The multiple vibration detection elements 208 are secured at the bottom surface of the gantry 202. Preferably, the multiple vibration detection elements 208 are electronic digital display height gauges, and the multiple vibration detection elements 208 serve to measure the height of the top surface of the protect bar 204. Electronic digital display height gauges are commercially available form the markets. The multiple vibration detection elements 208 may send the measured data to the controller 10 via cables. By means of the multiple vibration detection elements 208, the movement of the protect bar 204 along the vertical direction Z can be obtained by the controller 10. When the height of the protect bar 204 change in a short time (the rate of change is above predetermined rate), it is determined that the protect bar 204 is impeded by particular matter with a height above the predetermined height.

In the present invention, there is a gap 220 between the protect bar 204 and the glass substrate 100 to be detected, the gap 220 has a predetermined height (adjustable) corresponding with the mean value of the height of typical particulate matter. When the scanning light is emitted from the light emitter 300, the light receiver 400 will only receive a part of light if there is the particular matter in the gap 220. The digital signal of the light intensity can be analyzed by the light receiver 400 and the size of the particular matter can be calculated. Furthermore, the effective width of detection of the light receiver 400 can be set and changed as needed, so as to detect different kinds of particular matter.

In the present invention, the particulate matter detection apparatus further comprises multiple vibration detection elements 208. By means of the multiple vibration detection elements 208, the transparent or translucent particular matter can also be detected. Because the transparent or translucent particular matter will hit against the protect bar 204 and the protect bar 204 vibrates when the height of the transparent or translucent particular matter is above the predetermined height H of the gap 220. In this way, the transparent or translucent particular matter can also be detected.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A particulate matter detection apparatus, comprising a gantry, a protect bar, a light emitter and a light receiver, wherein the protect bar is coupled to the gantry, there is a gap between the protect bar and the glass substrate to be detected, the gap has a predetermined height, the light emitter and the light receiver are located at the opposite sides of the glass substrate respectively, the light emitter is configured to emit light towards the gap, the light receiver is configured to receive the light passing through the gap, wherein the particulate matter detection apparatus further comprises an actuator and a controller, the actuator serves to actuate the protect bar, the light emitter and the light receiver such that the protect bar, the light emitter and the light receiver move synchronously the controller serves to control the protect bar, the light emitter and the light receiver.

2. The particulate matter detection apparatus of claim 1, wherein the predetermined height is 100 micron to 800 micron.

3. The particulate matter detection apparatus of claim 1, wherein the predetermined height is 200 micron.

4. The particulate matter detection apparatus of claim 1, wherein the light emitter is laser transmitter.

5. The particulate matter detection apparatus of claim 1, wherein the light receiver is CCD image sensor.

6. The particulate matter detection apparatus of claim 1, wherein the particulate matter detection apparatus further comprises an alarm; the alarm is electrically connected to the controller, such that when the light receiver detects particulate matter, the alarm is enabled.

7. The particulate matter detection apparatus of claim 6, wherein the protect bar is coupled to the gantry by multiple bolts, the protect bar is provided with multiple counterbored through holes, the head portions of the multiple bolts are hooked in the multiple counterbored through holes, the threaded portions of the multiple bolts are engaged with the gantry.

8. The particulate matter detection apparatus of claim 7, wherein the particulate matter detection apparatus further comprises multiple compression springs which surround the multiple bolts, the compression springs abut against the bottom surface of the gantry and the top surface of the protect bar.

9. The particulate matter detection apparatus of claim 8, wherein the particulate matter detection apparatus further comprises multiple vibration detection elements, the multiple vibration detection elements serve to detect the vibration of the protect bar.

10. The particulate matter detection apparatus of claim 9, wherein the multiple vibration detection elements are electronic digital display height gauges, the multiple vibration detection elements serve to measure the height of the top surface of the protect bar.

* * * * *